(12) United States Patent
Suka et al.

(10) Patent No.: US 9,284,408 B2
(45) Date of Patent: Mar. 15, 2016

(54) METHOD FOR PRODUCING POLYALKYLENE GLYCOL DERIVATIVE WITH NARROW MOLECULAR WEIGHT DISTRIBUTION, AND ACETAL GROUP-CONTAINING ALCOHOL COMPOUND FOR USE THEREIN AND ALKALI METAL SALT THEREOF

(71) Applicant: Shin-Etsu Chemical Co., Ltd., Tokyo (JP)

(72) Inventors: Yuki Suka, Joetsu (JP); Yuji Harada, Joetsu (JP); Takeru Watanabe, Joetsu (JP); Osamu Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/596,685

(22) Filed: Jan. 14, 2015

(65) Prior Publication Data

US 2015/0197601 A1    Jul. 16, 2015

(30) Foreign Application Priority Data

Jan. 16, 2014    (JP) .................................. 2014-006074

(51) Int. Cl.
| | |
|---|---|
| C08G 65/32 | (2006.01) |
| C08G 65/26 | (2006.01) |
| C07C 43/315 | (2006.01) |
| A61K 47/48 | (2006.01) |
| C08G 65/322 | (2006.01) |
| C08G 65/325 | (2006.01) |
| C07C 217/08 | (2006.01) |
| C08L 71/02 | (2006.01) |

(52) U.S. Cl.
CPC ...... *C08G 65/2639* (2013.01); *A61K 47/48215* (2013.01); *C07C 43/315* (2013.01); *C07C 217/08* (2013.01); *C08G 65/322* (2013.01); *C08G 65/3255* (2013.01); *C08G 2650/44* (2013.01)

(58) Field of Classification Search
CPC ....................................................... C08L 71/03
USPC .................................................. 525/403, 405
See application file for complete search history.

(56) References Cited

U.S. PATENT DOCUMENTS

| | | | |
|---|---|---|---|
| 3,268,587 | A | 8/1966 | de Vries |
| 5,510,103 | A | 4/1996 | Yokoyama et al. |
| 5,789,490 | A | 8/1998 | Chang |
| 6,455,639 | B1 | 9/2002 | Yasukohchi et al. |
| 6,576,794 | B2 | 6/2003 | Fukushima et al. |

(Continued)

FOREIGN PATENT DOCUMENTS

| | | |
|---|---|---|
| EP | 0985697 A1 | 3/2000 |
| EP | 2586811 A1 | 5/2013 |

(Continued)

OTHER PUBLICATIONS

Extended European Search Report corresponding to European Application No. 15151528.5 dated Jun. 1, 2015.

(Continued)

*Primary Examiner* — Terressa Boykin
(74) *Attorney, Agent, or Firm* — Myers Bigel & Sibley

(57) ABSTRACT

A method for producing a narrow molecular weight distribution polyalkylene glycol derivative having an amino group at an end is provided and allows for polymerization of ethylene oxide under mild conditions with suppressed occurrence of diol polymer impurities includes at least the steps of polymerizing ethylene oxide by using a compound represented by the following general formula (2) and converting a polymer end to $R^3$:

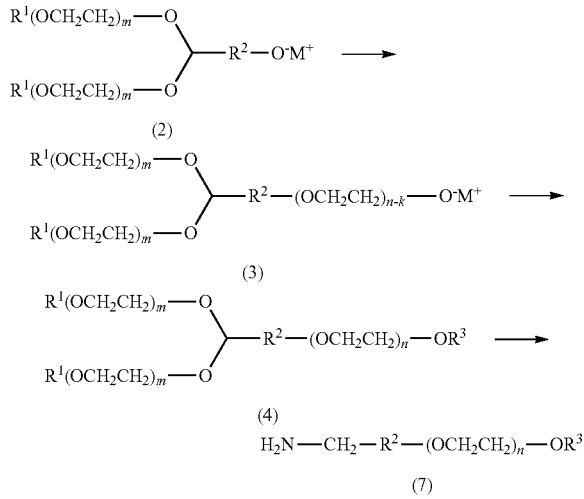

wherein $R^1$ represents a linear, branched, or cyclic monovalent hydrocarbon group having 1 to 10 carbon atoms;
$R^2$ represents a linear or branched divalent hydrocarbon group having 1 to 5 carbon atoms;
$R^3$ represents a linear, branched, or cyclic monovalent hydrocarbon group having 1 to 20 carbon atoms;
M represents sodium or potassium;
m represents an integer of 1 to 5;
n represents an integer of 1 to 450; and
k represents an integer of 1 to 5.

11 Claims, No Drawings

(56) References Cited

U.S. PATENT DOCUMENTS

| | | | |
|---|---|---|---|
| 7,728,175 B1 | 6/2010 | Qi et al. | |
| 2001/0000510 A1 | 4/2001 | Sakurai et al. | |
| 2010/0137206 A1 | 6/2010 | Lavasanifar et al. | |
| 2011/0028682 A1* | 2/2011 | Odaka et al. | 528/405 |
| 2011/0218322 A1 | 9/2011 | Nakamoto et al. | |
| 2011/0245509 A1 | 10/2011 | Nakamoto et al. | |

FOREIGN PATENT DOCUMENTS

| | | |
|---|---|---|
| JP | H08165343 A | 6/1996 |
| JP | 2690276 B2 | 12/1997 |
| JP | 2777530 B2 | 7/1998 |
| JP | 11-335267 | 12/1999 |
| JP | 3050228 | 6/2000 |
| JP | 3562000 | 6/2004 |
| WO | WO 97/30103 A2 | 8/1997 |
| WO | WO 03/040211 A2 | 5/2003 |
| WO | WO 2004/022630 A2 | 3/2004 |
| WO | WO 2008/071009 A1 | 6/2008 |
| WO | WO 2010/055866 A1 | 5/2010 |

OTHER PUBLICATIONS

Nagasaki et al. "Formyl-Ended Heterobifunctional Poly(ethylene oxide): Synthesis of Poly(ethylene oxide) with a Formyl Group at One End and a Hydroxyl Group at the Other End", *Bioconjugate Chem.* 6:231-233 (1995).

Extended European Search Report corresponding to European Application No. 15151526.9 dated Jun. 8, 2015.

* cited by examiner

METHOD FOR PRODUCING POLYALKYLENE GLYCOL DERIVATIVE WITH NARROW MOLECULAR WEIGHT DISTRIBUTION, AND ACETAL GROUP-CONTAINING ALCOHOL COMPOUND FOR USE THEREIN AND ALKALI METAL SALT THEREOF

RELATED APPLICATION

This application claims priority from Japanese Patent Application No. 2014-006074, filed Jan. 16, 2014, the disclosure of which is incorporated by reference herein in its entirety.

FIELD AND BACKGROUND OF THE INVENTION

The present invention relates to a method for producing a polyalkylene glycol derivative, with narrow molecular weight distribution, having an amino group at an end, and a new acetal group-containing alcohol compound for use therein and an alkali metal salt thereof.

Recently, in drug delivery systems, a method for encapsulating drugs in a polymer micelle using a block copolymer formed from a hydrophilic segment and a hydrophobic segment has been proposed (refer to, for example, Japanese Patent No. 2690276, Japanese Patent No. 2777530, and Japanese Patent Application Laid-Open No. 11-335267). By using this method, the polymer micelle functions as a carrier for drugs, producing various effects including sustained release in vivo and concentrated dosage at an affected region.

As the hydrophilic segment, many examples with use of a polyalkylene glycol skeleton have been proposed (refer to, for example, Japanese Patent No. 2690276, Japanese Patent No. 2777530, and Japanese Patent Application Laid-Open No. 11-335267). A compound having a polyalkylene glycol skeleton has low toxicity in vivo, and enables excretion by the kidney to be delayed. Consequently, in comparison with a compound having no polyalkylene glycol skeleton, the retention time in blood can be prolonged. As a result, with the use of a drug that is contained in a micelle of a polyalkylene glycol derivative, the dosage amount or dosage frequency can be reduced.

Among polyalkylene glycol derivatives, a compound having an amino group at an end can lead to a block copolymer composed of a polyalkylene glycol skeleton and an amino acid skeleton through a ring-opening polymerization reaction with α-amino acid-N-carboxyanhydride. Many examples with use of the produced block copolymer for encapsulating drugs in a polymer micelle have been proposed (refer to, for example, Japanese Patent No. 2690276, Japanese Patent No. 2777530, and Japanese Patent Application Laid-Open No. 11-335267).

Synthesis methods of such polyalkylene glycol derivatives having an amino group at an end are also known (refer to, for example, Japanese Patent No. 3050228 and Japanese Patent No. 3562000). In these methods, after polymerization of alkylene oxide with use of a metal salt of monohydric alcohol as a polymerization initiator, a polymer end is converted to a hydroxyl group, and then to a 2-cyanoethoxy group, finally leading to an amino group-containing substituent group (3-amino-1-propoxy group) through hydrogen reduction of the cyano group.

As a synthesis method of polyalkylene glycol derivatives having an amino group, a synthesis example by a reductive amination reaction is also reported. In the method, after polymerization of ethylene oxide with use of a potassium salt of 3,3-diethoxypropanol, the acetal end of the produced polymer is converted to a formyl group. Further, the polymer end leads to an amino group through a reductive amination reaction (refer to, for example, International Publication WO 2008/71009).

In regard to polyalkylene glycol having a formyl group at an end, many synthesis examples with use of an alkali metal salt of 3,3-diethoxypropanol are reported in the literature other than described above (refer to, for example, Bioconj. Chem. 1995, 6(2), 231-233 and International Publication WO 2010/55866). In these methods, however, the polymerization reaction requires a time for completion of 1 day or more, under conditions of high temperature and high pressure.

SUMMARY OF THE INVENTION

As disclosed in Bioconj. Chem. 1995, 6(2), 231-233 and WO 2010/55866, it is difficult to completely dissolve the metal salts of monohydric alcohol for use as a polymerization initiator in THF in many cases. In order to dissolve the metal salts in polymerization solvent, a co-solvent such as methanol and ethanol is required. Due to the presence of these alcohols in a reaction system, however, reduction in the polymerization rate is unavoidable. Consequently, crucial reaction conditions such as high temperature and high pressure are required for increasing the polymerization rate.

Monohydric alcohols contain a trace amount of water in many cases. The polymerization of alkylene oxide with a polymerization initiator prepared in a water-containing state produces a polymer compound having a hydroxyl group at both ends as by-product (hereinafter abbreviated as diol polymer). In the case of monohydric alcohols having a boiling point sufficiently higher than that of water, the water content can be reduced by dehydration under reduced pressure. Since methanol for use in a case in which an end is a methyl group has a boiling point lower than that of water, the water content cannot be removed by dehydration under reduced pressure. The polymerization with a metal salt prepared by using methanol, therefore, unavoidably produces a diol polymer. Since various physical properties of diol polymer such as structure and molecular weight are similar to those of the target substance, is extremely difficult to separate and purify. When the subsequent reactions proceed in the presence of diol polymer as impurity, a polymer including an amino group at both ends is produced unless proper reaction conditions are selected. The direct use of the polymer which includes such an impurity may result in the possibility that an intended performance cannot be achieved in designing a polymer micellizing agent. In the polymerization reaction, therefore, the water content is required to be reduced as low as possible.

In a synthesis method of an amino group-containing polyalkylene glycol derivative by reductive amination reaction, high-efficiency polymerization under mild conditions and removal of diol polymer impurity are fundamentally required. A polymerization method which satisfies both of the requirements is therefore desired to be developed.

Through intensive research for achieving the object, the present inventors found that use of a new compound described in detail in the following as a polymerization initiator accomplishes the polymerization of ethylene oxide under mild conditions and the suppression of formation of diol polymers, eventually leading to narrow molecular weight distribution polyalkylene glycol derivatives having an amino group at an end. The present invention has been thus accomplished.

More specifically, the present invention provides a method for producing a narrow molecular weight distribution polyalkylene glycol derivative having an amino group at an end represented by a general formula (7) by using a compound represented by the following general formula (2) as a polymerization initiator:

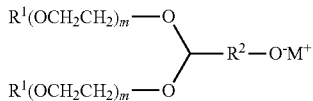
(2)

wherein $R^1$ each independently represents a linear, branched, or cyclic monovalent hydrocarbon group having 1 to 10 carbon atoms;
$R^2$ represents a linear or branched divalent hydrocarbon group having 1 to 5 carbon atoms;
m each independently represents an integer of 1 to 5; and
M represents sodium or potassium;

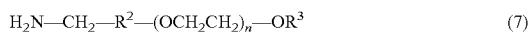
$$H_2N-CH_2-R^2-(OCH_2CH_2)_n-OR^3 \qquad (7)$$

wherein $R^2$ is the same as defined in the general formula (2);
$R^3$ represents a linear, branched, or cyclic monovalent hydrocarbon group having 1 to 20 carbon atoms; and
n represents an integer of 1 to 450.
The method comprises the steps of:
a) reacting a compound represented by the formula (2) with ethylene oxide;
b) reacting a reaction product of the step a) with a compound represented by a general formula (8):

$$R^3(OCH_2CH_2)_k X \qquad (8)$$

wherein $R^3$ is the same as defined in the general formula (7);
k represents an integer of 0 to 5; and
X represents a halogen atom or a leaving group; and
c) reductively aminating the reaction product of the step b).

The present invention in another embodiment provides a method for producing a narrow molecular weight distribution polyalkylene glycol derivative having an amino group at an end represented by the general formula (7) comprises the steps of:
1) a step of reacting a compound represented by the following general formula (2) with ethylene oxide in an organic solvent to obtain a compound represented by the following general formula (3):

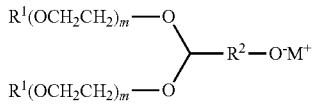
(2)

wherein $R^1$ each independently represents a linear, branched, or cyclic monovalent hydrocarbon group having 1 to 10 carbon atoms;
$R^2$ represents a linear or branched divalent hydrocarbon group having 1 to 5 carbon atoms;
m each independently represents an integer of 1 to 5; and
M represents sodium or potassium.

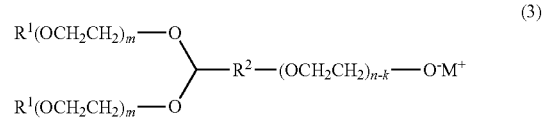
(3)

wherein $R^1$, $R^2$, m, and M are the same as defined in the general formula (2);
n represents an integer of 1 to 450; and
k represents an integer of 0 to 5;
2) a step of reacting a compound represented by the following general formula (3) with a compound represented by the following general formula (8) to obtain a compound represented by the following general formula (4):

$$R^3(OCH_2CH_2)_k X \qquad (8)$$

wherein k is the same as defined in the general formula (3);
$R^3$ represents a linear, branched, or cyclic monovalent hydrocarbon group having 1 to 20 carbon atoms; and
X represents a halogen atom or a leaving group;

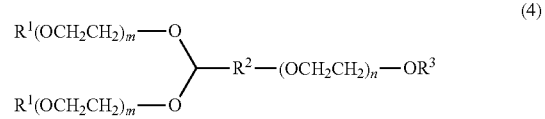
(4)

wherein $R^1$, $R^2$, m, and n are the same as defined in the general formula (3); and
$R^3$ is the same as defined in the general formula (8);
3) a step of reacting a compound represented by the general formula (4) with water in the presence of an acid catalyst to obtain a compound represented by the following general formula (5):

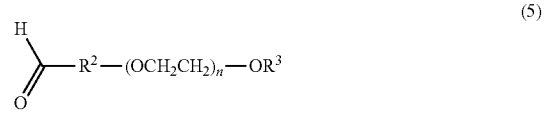
(5)

wherein $R^2$, $R^3$, and n are the same as defined in the general formula (4);
4) a step of reacting a compound represented by the general formula (5) with ammonia or hydroxylamine to obtain a compound represented by the following general formula (6):

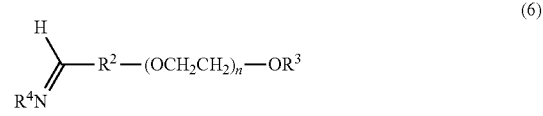
(6)

wherein $R^2$, $R^3$, and n are the same as defined in the general formula (5); and
$R^4$ represents a hydrogen atom or a hydroxyl group; and
5) a step of producing a compound represented by the following general formula (7) by a reduction reaction of a compound represented by the general formula (6):

$$H_2N-CH_2-R^2-(OCH_2CH_2)_n-OR^3 \qquad (7)$$

wherein $R^2$, $R^3$, and n are the same as defined in the general formula (6).

The present invention in another embodiment relates to an acetal group-containing alcohol compound represented by the following formula (1):

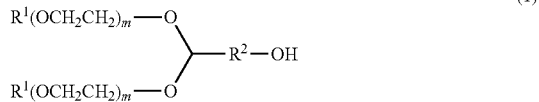

wherein $R^1$ each independently represents a linear, branched, or cyclic monovalent hydrocarbon group having 1 to 10 carbon atoms;
$R^2$ represents a linear or branched divalent hydrocarbon group having 1 to 5 carbon atoms; and
m each independently represents an integer of 1 to 5.

The present invention in another embodiment relates to a metal salt of an acetal group-containing alcohol compound represented by the following formula (2):

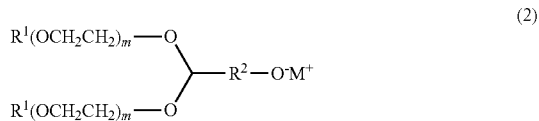

wherein $R^1$ each independently represents a linear, branched, or cyclic monovalent hydrocarbon group having 1 to 10 carbon atoms;
$R^2$ represents a linear or branched divalent hydrocarbon group having 1 to 5 carbon atoms;
m each independently represents an integer of 1 to 5; and
M represents sodium or potassium.

The method of the present invention for producing a narrow molecular weight distribution polyalkylene glycol derivative having an amino group at an end enables the polymerization of ethylene oxide under conditions milder than conventional ones and the suppression of formation of impurities due to a trace amount of water, and thereby being capable of producing a narrow molecular weight distribution polyalkylene glycol derivative having an amino group at an end. This method requires no freeze drying in purification and extraction of a polyalkylene glycol derivative, enabling an industrial-scale production of polyalkylene glycol derivatives with further advantages of simplified facilities and processes. Further, the polyalkylene glycol derivative produced by the production method of the present invention has a narrow molecular weight distribution, capable of being extremely advantageously used in leading to a block copolymer formed from a hydrophilic segment and a hydrophobic segment, for use in a field of drug delivery system. Furthermore, the new acetal group-containing alcohol compound and the alkali metal salt thereof of the present invention are extremely useful, being used as a more useful polymerization initiator, i.e. a substitute for a conventional one, in the production method of the present invention.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

A method for producing a narrow molecular weight distribution polyalkylene glycol derivative having an amino group at an end according to an embodiment of the present invention includes the following [Step 1] and [Step 2], and a step of reductively aminating the reaction product of the [Step 2]. Alternatively, an aspect of the present invention preferably includes the following [Step 1] to [Step 5]. The narrow molecular weight distribution polyalkylene glycol derivative having an amino group at an end produced by the production method according to the present embodiment is represented by the following formula (7):

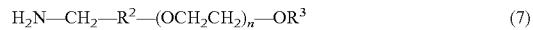

wherein $R^2$ represents a linear or branched divalent hydrocarbon group having 1 to 5 carbon atoms;
$R^3$ represents a linear, branched, or cyclic monovalent hydrocarbon group having 1 to 20 carbon atoms; and
n represents an integer of 1 to 450.

Specific examples of the $R^2$ representing a linear or branched, saturated divalent hydrocarbon group having 1 to 6 carbon atoms include a group with a hydrogen atom removed from any one of a methyl group, an ethyl-group, an n-propyl group, an isopropyl group, an n-butyl group, an isobutyl group, a tert-butyl group, an n-pentyl group, and n-hexyl group.

Specific examples of the $R^3$ representing a linear, branched, or cyclic, saturated or unsaturated monovalent hydrocarbon group having 1 to 20 carbon atoms include a methyl group, an ethyl-group, an n-propyl group, an isopropyl group, an n-butyl group, an isobutyl group, a tert-butyl group, a pentyl group, a cyclopentyl group, a hexyl group, a cyclohexyl group, an octyl group, a decyl group, a dodecyl group, a phenyl group, an o-tolyl group, a m-tolyl group, a p-tolyl group, a 2,3-xylyl group, a 2,4-xylyl group, a 2,5-xylyl group, a 2,6-xylyl group, a 3,4-xylyl group, a 3,5-xylyl group, a mesityl group, a vinyl group, and allyl group, although this is not particularly limited thereto.

The n represents an integer of, for example, 1 to 450, preferably n=10 to 400, more preferably n=20 to 350. The term "molecular weight" and "dispersity" of a polymer as used in the present specification mean measured values by gel permeation chromatography (hereinafter abbreviated as GPC), respectively. The compound represented by the general formula (7) produced by the production method of the present invention has a narrow molecular weight distribution, having a dispersity of, for example, 1.0 to 1.4, preferably 1.0 to 1.3, more preferably 1.0 to 1.2.

In selection of each compound for use in each of the steps of the following production method, desired $R^2$, $R^3$, and n can be selected such that a compound represented by the general formula (7) can be obtained as desired final product.

Prior to the [Step 1] to the [Step 5], a [Preceding Step 1] and a [Preceding Step 2] may be performed as optional steps. In the [Preceding Step 1] and the [Preceding Step 2], a compound as a polymerization initiator represented by the general formula (2) for use in the production method of polyethylene glycol derivatives including the [Step 1] to the [Step 5] and a compound as the raw material (starting material) thereof represented by the general formula (1) are produced. In the following description of the embodiments, the [Preceding step 1] and a [Preceding Step 2] and the [Step 1] to the [Step 5] are sequentially described in the time-series order.

The [Preceding Step 1] is a step of synthesizing a compound represented by the following general formula (1):

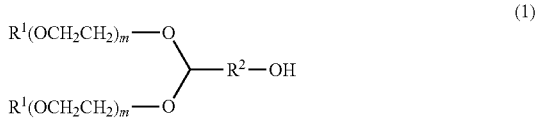

wherein $R^1$ represents a linear, branched, or cyclic monovalent hydrocarbon group having 1 to 10 carbon atoms;

$R^2$ represents a linear or branched divalent hydrocarbon group having 1 to 5 carbon atoms; and m represents an integer of 1 to 5.

Specific examples of the $R^1$ representing a monovalent hydrocarbon group include a methyl group, an ethyl-group, an n-propyl group, an isopropyl group, an n-butyl group, an isobutyl group, a tert-butyl group, a pentyl group, a cyclopentyl group, a hexyl group, a cyclohexyl group, an octyl group, a decyl group, and a dodecyl group, although this is not particularly limited thereto. Specific examples of the $R^2$ representing a linear or branched divalent hydrocarbon group having 1 to 6 carbon atoms are the same as described in the general formula (7) as final target compound.

The compound represented by the general formula (1) may be produced by, for example, the following steps, although this is not particularly limited thereto. For example, even with the change in the sequence of an acetal exchange reaction for synthesizing (1-1) and a substitution reaction with potassium acetate for synthesizing (1-2), the compound represented by the general formula (1) may be produced.

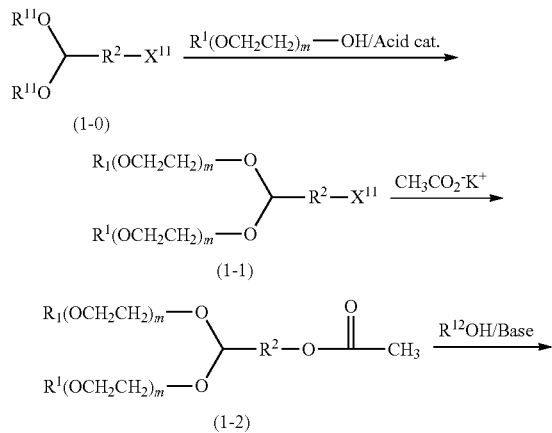

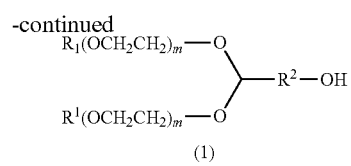

wherein $R^1$, $R^2$, and m are the same as defined in the general formula (1); $R^{11}$ and $R^{12}$ each independently represent a linear, branched, or cyclic monovalent hydrocarbon group having 1 to 10 carbon atoms; and $X^{11}$ represents a halogen atom or a leaving group.

In a first phase of the [Preceding Step 1], the exchange reaction of an acetal side chain is performed in the presence of an acid catalyst to obtain a compound represented by the general formula (1-1). Specific examples of the monovalent hydrocarbon group represented by $R^{11}$ in a starting material represented by the general formula (1-0) include a methyl group, an ethyl-group, an n-propyl group, an isopropyl group, an n-butyl group, an isobutyl group, a tert-butyl group, a pentyl group, a cyclopentyl group, a hexyl group, a cyclohexyl group, an octyl group, a decyl group, and a dodecyl group, although this is not particularly limited thereto.

In a compound represented by the general formula (1-1), $X^{11}$ represents a halogen atom or a leaving group. Specific examples of the halogen atom include F, Cl, Br, and I. Specific examples of the elimination group include a p-toluenesulfonyloxy group, a methanesulfonyloxy group, a trifluoromethane sulfonyloxy group, an acyloxy group, a phenoxy group, and alkoxy group, although this is not particularly limited thereto.

In the acetal exchange reaction, a starting material represented by the general formula (1-0) is reacted with a compound represented by the general formula $R^1(OCH_2CH_2)_m$OH in the presence of an acid catalyst without a solvent or as needed in a proper solvent. On this occasion, the produced $R^{11}$OH is distilled away under heating or under reduced pressure such that the equilibrium is shifted to the product side for higher yield. The amount of a compound represented by the general formula $R^1(OCH_2CH_2)_m$OH used is, for example, 2 to 100 equivalents, preferably 2 to 50 equivalents, more preferably 2 to 20 equivalents, relative to the number of moles of the starting material as a reactive substrate although this is not particularly limited thereto.

Specific examples of the acid catalyst include carboxylic acids such as formic acid, acetic acid, propionic acid, succinic acid, citric acid, tartaric acid, fumaric acid, malic acid, and trifluoroacetic acid, inorganic acids such as hydrochloric acid, sulfuric acid, nitric acid, phosphoric acid, and perchloric acid, and sulfonic acids such as benzenesulfonic acid, and p-toluenesulfonic acid, although not limited thereto. Specifically, a solid acid such as AMBERLYST SERIES made by Organo Corporation may be used. The amount of the acid catalyst used is, for example, 0.001 to 10 equivalents, preferably 0.001 to 5 equivalents, more preferably 0.001 to 2 equivalents, relative to the number of moles of the starting material as a reactive substrate.

In performing the acetal exchange reaction, a solvent can be used. Examples of the solvent include ethers such as THF and 1,4-dioxane, and aromatic hydrocarbons such as benzene, toluene, and xylene, and the acetonitrile, although this is not limited thereto. These solvents may be used singly or in combinations of two or more. In that case, the mixing ratio is not particularly limited. The amount of the solvent used is, for example, 1 to 50 times, preferably 2 to 10 times, more preferably 2 to 5 times the mass of the starting material as a reactive substrate, although this is not particularly limited. The reaction may be performed at a temperature of, for example, room temperature to 100° C., preferably at a temperature of 50 to 80° C. The reaction system may be cooled or heated as needed.

The reaction time of acetal exchange reaction is, for example, about 0.1 to 100 hours. Preferably the reaction is monitored by gas chromatography (GC), thin-layer chromatography (TLC), or the like to be completed. The reaction product mixture which includes a compound represented by the general formula (1-1) may be purified by a normal aqueous treatment (aqueous work-up). As needed, filtration may be performed for removal of the salts or insoluble matters produced by the reaction. Alternatively, corresponding to the physical properties of the target compound represented by the general formula (1-1), purification may be performed by common procedures such as distillation, chromatography, and recrystallization.

In a second phase of the [Preceding Step 1], a compound represented by the general formula (1-1) is reacted with potassium acetate. The amount of potassium acetate used is, for example, 1 to 20 equivalents, preferably 1 to 10 equivalents, more preferably 1 to 5 equivalents, relative to the number of moles of a compound represented by the general formula (1-1) as a reactive substrate, although this is not particularly limited. The reaction may be performed in a proper solvent. Specific examples of the solvent include ethers such as THF and 1,4-dioxane, and aromatic hydrocarbons such as benzene, toluene, and xylene, acetonitrile, and N-methylpyrrolidone, although this is not limited thereto.

In order to improve the reaction rate, an iodide such as sodium iodide, lithium iodide, and tetrabutylammonium iodide, or a bromide such as sodium bromides, lithium bromides, and tetrabutylammonium bromide may be added as a catalyst. The amount of the catalyst added is, for example, 0.001 to 2 equivalents, preferably 0.005 to 0.5 equivalents, relative to the number of moles of a compound represented by the general formula (1-1) as a reactive substrate.

The reaction in the second phase may be performed at a temperature of, for example, room temperature to 150° C. The reaction system may be heated or cooled as needed. The reaction time may be, for example, about 0.1 to 100 hours, in the same way as in the first phase. Preferably the reaction is monitored by gas chromatography (GC), thin-layer chromatography (TLC), or the like to be completed. The reaction product mixture which includes a compound represented by the general formula (1-2) may be purified by a normal aqueous treatment (aqueous work-up). As needed, filtration may be performed for removal of the salts or insoluble matters produced by the reaction. Alternatively, corresponding to the physical properties of the target compound represented by the general formula (1-2), purification may be performed by common procedures such as distillation, chromatography, and recrystallization.

In a third phase of the [Preceding Step 1], an ester exchange reaction between a compound represented by the general formula (1-2) and a compound represented by the general formula $R^{12}OH$ is performed in the presence of a base catalyst to obtain a compound represented by the general formula (1). Specific examples of the monovalent hydrocarbon group $R^{12}$ include a methyl group, an ethyl-group, an n-propyl group, an isopropyl group, an n-butyl group, an isobutyl group, a tert-butyl group, a pentyl group, a cyclopentyl group, a hexyl group, a cyclohexyl group, an octyl group, a decyl group, and a dodecyl group, although this is not limited thereto. The amount of the compound represented by the general formula $R^{12}OH$ used is, for example, 1 to 100 equivalents, preferably 1 to 50 equivalents, more preferably 1 to 20 equivalents, relative to the number of moles of the compound represented by the general formula (1-2) as a reactive substrate, although this is not particularly limited.

Examples of the base catalyst for use in the third phase include: hydroxides such as sodium hydroxide, potassium hydroxide, and tetramethylammonium hydroxide; carbonates such as sodium carbonate, potassium carbonate, and cesium carbonate; metal alkoxides such as sodium methoxide, sodium ethoxide, and potassium t-butoxide; metal hydrides such as sodium hydride and potassium hydride; primary, secondary and tertiary aliphatic amines; mixed amines; aromatic amines; heterocyclic amines; and ammonia water, although this is not limited thereto.

Examples of the primary aliphatic amines include methylamine, ethylamine, n-propylamine, isopropylamine, n-butylamine, isobutylamine, sec-butylamine, tert-butylamine, and ethylene diamine; examples of the secondary aliphatic amines include dimethylamine, diethylamine, di-n-propylamine, diisopropylamine, di-n-butylamine, diisobutylamine, di-sec-butylamine; examples of the tertiary aliphatic amines include trimethylamine, triethylamine, tri-n-propylamine, triisopropylamine, tri-n-butylamine, tri-isobutylamine, and tri-sec-butylamine; examples of the mixed amines include dimethylethylamine, methylethylpropylamine, benzylamino, phenethylamine, benzyldimethylamine; specific examples of the aromatic amines and the heterocyclic amines include aniline derivatives (e.g. aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, and pyridine derivatives (e.g. pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), although this is not limited thereto. The amount of the base catalyst used is, for example, 0.1 to 10 times, preferably 0.5 to 5 times the number of moles of a compound represented by the general formula (1-2) as a reactive substrate.

In the ester exchange reaction, the produced $CH_3CO_2R^{12}$ is distilled away under heating or under reduced pressure such that the equilibrium is shifted to the product side for higher yield. In performing the reaction, a solvent can be used. Specific examples of the solvent include ethers such as THF and 1,4-dioxane, and aromatic hydrocarbons such as benzene, toluene, and xylene, and the acetonitrile, although this is not limited thereto. These solvents may be used singly or in combinations of two or more. In that case, the mixing ratio is not particularly limited. The amount of the solvent used is, for example, 1 to 50 times, preferably 2 to 10 times, more preferably 2 to 5 times the mass of a compound represented by the general formula (1-2) as a reactive substrate, although this is not particularly limited. The reaction may be performed at a temperature of, for example, room temperature to 100° C., preferably at a temperature of room temperature to 60° C. The reaction system may be cooled or heated as needed.

The reaction time of ester exchange reaction may be, for example, about 0.1 to 100 hours. Preferably the reaction is monitored by gas chromatography (GC), thin-layer chromatography (TLC), or the like to be completed. The reaction product mixture which includes a compound represented by the general formula (1) may be purified by a normal aqueous treatment (aqueous work-up). As needed, filtration may be performed for removal of the salts or insoluble matters produced by the reaction. Alternatively, corresponding to the physical properties of the target compound represented by the general formula (1), purification may be performed by common procedures such as distillation, chromatography, and recrystallization.

In the [Preceding Step 2], a compound represented by the general formula (1) is reacted with an alkali metal compound selected from M, $M^+H^-$, and $R^{21}O^-M^+$ (wherein M represents sodium (Na) or potassium (K), and $R^{21}$ represents a monovalent alkyl group having 1 to 6 carbon atoms) to obtain a compound represented by the general formula (2):

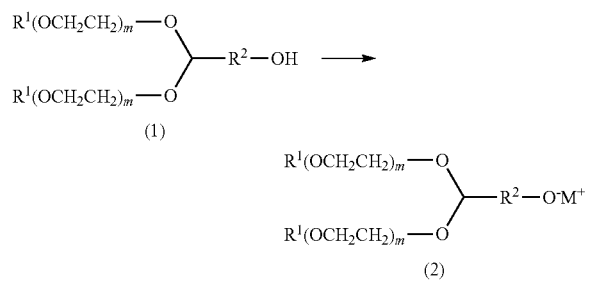

wherein $R^1$, $R^2$, and m are the same as defined in the formula (1), and M is the same as defined for the alkali metal compound.

In the [Preceding Step 2], the alkali metal compound to be reacted with a compound represented by the general formula (1) means a substance selected from the group consisting of an alkali metal represented by M, a hydride of alkali metal represented by $M^+H^-$, and an alkali metal salt of monohydric alcohol represented by $R^{21}O^-M^+$ (wherein M represents sodium or potassium, and $R^{21}$ represents a monovalent alkyl group having 1 to 6 carbon atoms). Specific examples of the $R^{21}$ include a methyl group, an ethyl-group, an n-propyl group, an isopropyl group, an n-butyl group, a sec-butyl group, a tert-butyl group, an n-pentyl group, an isopentyl group, and a hexyl group, although this is not limited thereto. The amount of an alkali metal, $M^+H^-$, or $R^{21}O^-M^+$ used is, for example, 0.5 to 3.0 equivalents, preferably 0.8 to 2.0 equivalents, more preferably 0.9 to 1.5 equivalents, relative to the number of moles of a compound represented by the general formula (1).

In synthesizing a compound represented by the general formula (2) in the [Preceding Step 2], a proper solvent can be used as needed. Specific examples of the solvent include ethers such as THF and 1,4-dioxane, and aromatic hydrocarbons such as benzene, toluene, and xylene, although this is not limited thereto. In the case of using a solvent, use of a solvent distilled with a dehydrating agent such as sodium metal is preferred. The solvent has a water content ratio of, for example, 50 ppm or less, preferably 10 ppm or less, more preferably 5 ppm or less. The amount of the solvent used is, for example, 1 to 50 times, preferably 2 to 10 times, more preferably 2 to 5 times the mass of a compound represented by the general formula (1) although this is not particularly limited thereto. The reaction may be performed at a temperature of −78 to 100° C., preferably at a temperature of 0° C. to the reflux temperature of the solvent for use. The reaction system may be cooled or heated as needed.

As described above, the polymerization of alkylene oxide with a polymerization initiator prepared in a reaction system with a water-containing monohydric alcohol produces a diol polymer as by-product. Separation of a diol polymer from the target substance is extremely difficult. There is a high probability that the intended performance of a polymer micellizing agent is not achieved with the direct use of the polymer which contains a diol polymer or impurities derived therefrom. In the polymerization reaction, therefore, the water content in the reaction system including a compound (polymerization initiator) represented by the general formula (2) is required to be reduced as low as possible. A compound represented by the general formula (1) with, for example, $R^1$=methyl group, $R^2$=$CH_2CH_2$, m=1, and a high boiling point of 102° C. (30 Pa), has a sufficient difference in boiling point from water, so that separation of water can be achieved by drying under reduced pressure. In that case, prior to addition of an alkali metal compound, the compound represented by the general formula (1) is sufficiently dried under reduced pressure and then distilled, so that the water content ratio is reduced, for example, to 50 ppm or less, preferably 10 ppm or less, more preferably 5 ppm or less, for the reaction to proceed.

After completion of the preceding step 2, preferably the reaction is performed to have a mass ratio between a compound represented by the general formula (1) and a compound represented by the general formula (2) of 0:100 to 20:80. The mass ratio can be achieved under the reaction conditions described above. In the step 2 of the present invention, a potassium salt represented by the general formula (2) is not required to be 100% generated, with a raw material alcohol represented by the general formula (1) being remained (in the case of the mass ratio of a compound represented by the general formula (1)>0). Even when the complete conversion of raw material alcohol (1) to a potassium salt (2) cannot be achieved, the raw material alcohol (1) functions also as a solvent of the potassium salt (2), so that the polymerization proceeds smoothly. Alternatively, achieving the complete consumption of raw material alcohol (1) (in the case of a mass ratio of the compound represented by the general formula (1) to the compound represented by the general formula (2) of 0:100) has an advantage that the step 1 can be performed without use of an alcohol co-solvent as described below.

The preceding step 1 and the preceding step 2 are optional steps. Subsequently the polymerization reaction of ethylene oxide is performed, using a compound represented by the general formula (2) as a polymerization initiator.

In the [Step 1], a compound represented by the general formula (2) is completely dissolved in an organic solvent and then reacted with ethylene oxide at a reaction temperature of, for example, 30 to 60° C. In performing the step 1, a compound represented by the following general formula (3) can be produced:

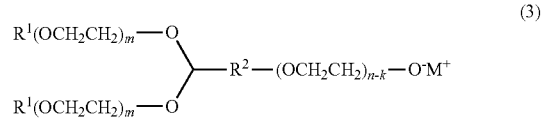

wherein $R^1$, $R^2$, and M are the same as defined in the general formula (2);

n represents an integer of 1 to 450; and k represents an integer of 0 to 5.

The [Step 1] is performed in an organic solvent. In particular, a cyclic ether compound having 4 to 10 carbon atoms is preferred for use as the organic solvent. Specific examples of the cyclic ether include furan, 2,3-dihydrofuran, 2,5-dihydrofuran, 2,3-dimethylfuran, 2,5-dimethylfuran, tetrahydrofuran (THF), 2-methyltetrahydrofuran, 3-methyltetrahydrofuran, 2,5-dimethyltetrahydrofuran, 1,2-methylenedioxybenzene, 1,3-dioxolane, 2-methyl-1,3-dioxolane, 4-methyl-1,3-dioxolane, 2,2-dimethyl-1,3-dioxolane, 3,4-dihydro-2H-pyran, tetrahydropyran, 1,3-dioxane, 1,4-dioxane, 2,4-dimethyl-1,3-dioxane, 1,4-benzodioxan, 1,3,5-trioxane, and oxepane, although this is not limited thereto. Alternatively, an organic solvent other than a cyclic ether compound may be used. Specific examples thereof include aromatic hydrocarbons such as benzene, toluene, and xylene, and a linear or branched ether compound such as diglyme, although this is not limited thereto. The organic solvent for use in the [Step 1] may be a single solvent or a combination of two or more. In the case of combination, the combination of compounds and the mixing ratio thereof are not limited.

The amount of the organic solvent for use in the [Step 1] is, for example, 1 to 50 times, preferably 2 to 30 times, more preferably 3 to 20 times the mass of ethylene oxide for use, though not particularly limited. Preferably the organic solvent for use is distilled with a dehydrating agent such as sodium metal. The water content ratio is, for example, 50 ppm or less, preferably 10 ppm or less, more preferably 5 ppm or less.

A single sodium salt or potassium salt commonly used as conventional polymerization initiator is hardly dissolved in THF in many cases. In that case, a co-solvent such as methanol and ethanol is required for homogeneous polymerization. Due to the presence of these alcohols in a reaction system, however, reduction in the polymerization rate is unavoidable. Consequently, crucial reaction conditions such as high temperature and high pressure are required for increasing the polymerization rate. In contrast, the new acetal group-containing alcohol derivative represented by the general formula (2) for use as a polymerization initiator in the present invention is easily dissolved in cyclic ether compounds including THF without requiring a co-solvent of alcohols, being advantageously used for achieving polymerization under mild conditions. Accordingly the [Step 1] in the present invention is performed preferably without using an alcohol co-solvent.

As the addition method of ethylene oxide to a reaction system, ethylene oxide may be added in one batch or in successive portions to a reaction system in which a compound represented by the general formula (2) is dissolved in an organic solvent. Alternatively the solution of ethylene oxide dissolved in the organic solvent may be dripped into a reaction system. The polymerization is performed at a temperature of, for example, 30 to 60° C., preferably 40 to 60° C., more preferably 45 to 60° C. The degree of progress of polymerization reaction can be monitored with GPC. When no change is observed in conversion ratio of ethylene oxide, the completion can be assumed.

In the [Step 2], a compound represented by the general formula (3) is reacted with a compound represented by the following general formula (8). In performing the step 2, a compound represented by the following formula (4) is produced.

(8)

wherein k is the same as defined in the general formula (3);

$R^3$ represents a linear, branched, or cyclic monovalent hydrocarbon group having 1 to 20 carbon atoms; and X represents a halogen atom or a leaving group.

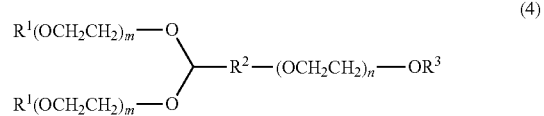
(4)

wherein $R^1$, $R^2$, m, and n are the same as defined in the general formula (3); and $R^3$ is the same as defined in the general formula (8).

Specific examples of the monovalent hydrocarbon group $R^3$ are the same as described in the formula (7), and the $R^3$ of formula (8) can be selected such that the $R^3$ of a desired final product can be obtained.

The k of a compound represented by the general formula (8) is an integer of 0 to 5. A compound with k=0 may have a low boiling point with difficulty in handling, or high toxicity in some cases. Accordingly, a compound with k=1 to 5 is preferred, and a compound with k=1 to 3 is more preferred.

In synthesizing a compound represented by the general formula (4) in the [Step 2], a compound represented by the general formula (8) may be directly added into a reaction liquid (reaction liquid including (3)) after completion of the reaction in the [Step 1], or a compound represented by the general formula (8) dissolved in a proper solvent may be used as needed. Specific examples of the solvent include ethers such as THF and 1,4-dioxane, and aromatic hydrocarbons such as benzene, toluene, and xylene. The amount of the solvent used is, for example, 1 to 50 times, preferably 2 to 10 times, more preferably 2 to 5 times the mass of the compound represented by the general formula (8), although this is not particularly limited. The reaction may be performed at a temperature of, for example, 0 to 100° C., preferably at a temperature of 40 to 70° C. The reaction system may be cooled or heated as needed. The amount of a compound represented by the general formula (8) used is, for example, 1 to 50 equivalents, preferably 1 to 20 equivalents, more preferably 1 to 10 equivalents, relative to the number of moles of a compound represented by the general formula (3). The degree of progress of the reaction can be monitored by $^1$H-NMR, and when the peak derived from a hydroxyl group occurring due to quenching of the reaction liquid with water disappears, the completion can be assumed.

The reaction of the [Step 2] can be accelerated with a base catalyst. The base catalyst may be the same as those exemplified in the third phase of the preceding step 1. The amount of the base catalyst used is for example, 0.1 to 10 times, preferably 0.5 to 5 times the number of moles of a compound represented by the general formula (3).

In the [Step 2], in order to separate a compound represented by the general formula (3) from an alkali metal salt produced by a reaction with a compound represented by the general formula (8), an alkali adsorbent may be further used. Examples of the preferable alkali adsorbent for use include a synthesized magnesium silicate (e.g. KYOWADO 600 made by Kyowa Chemical Industry Co., Ltd.) and a synthesized aluminum silicate (e.g. KYOWADO 700 made by Kyowa Chemical Industry Co., Ltd.), although this is not limited thereto. The amount of the alkali adsorbent used is for example, 0.1 to 10 times, preferably 0.2 to 8 times, more preferably 0.3 to 6 times the mass of a compound represented by the general formula (4). On the completion of the reaction of a compound represented by the general formula (3) and a compound represented by the general formula (8), the alkali adsorbent is directly fed into the reaction liquid for the reaction to proceed for 0.5 to 6 hours. After completion of the reaction, the alkali adsorbent can be removed by filtration.

In the case of a compound represented by the general formula (4) in a solid form, the solid may be extracted for use prior to the subsequent step. In that case, the reaction liquid is, either directly or after concentration, dripped into a poor solvent to be crystallized. In the case of concentration, the concentration of a compound represented by the general formula (4) is adjusted to be, for example, 10 to 50 mass %, preferably 15 to 45 mass %, more preferably 20 to 40 mass %.

In concentration, solvent substitution with a good solvent for a compound represented by the general formula (4) may be performed for crystallization. In that case, examples of the good solvent include ethers such as 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. These solvents may be used singly or in combinations of two or more. In that case, the mixing ratio is not particularly limited. The concentration after solvent substitution is, for example, 10 to 50 mass %, preferably 15 to 45 mass %, more preferably 20 to 40 mass %.

The poor solvent for use has a low solubility for a compound represented by the general formula (4). Examples of the suitable poor solvent for use include hydrocarbons such as hexane, heptane, octane, nonane, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (4), although this is not particularly limited thereto. The poor solvents may be used alone, or may be used by being mixed with a different solvent. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, although this is not limited thereto.

In the [Step 2], after precipitation of solid by crystallization, the solid may be washed for purification as needed. The solvent for use in washing is preferably the same poor solvent as described above, although this is not particularly limited, without particular limitation on the amount of the washing solvent used. The produced solid is dried under reduced pressure, so that a compound represented by the general formula (4) can be extracted as solid.

In the [Step 3] and the subsequent steps, the reaction product in the step 2 is reductively aminated to obtain a compound represented by the general formula (7). In the step 3, specifically, a compound represented by the general formula (4) is reacted with water in the presence of an acid catalyst, so that a compound represented by the following general formula (5) can be synthesized.

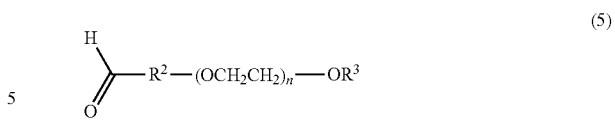

wherein, $R^2$, $R^3$, and n are the same as defined in the general formula (4).

In the reaction for synthesizing a compound represented by the general formula (5), a compound represented by the general formula (4) is reacted with water in the presence of an acid catalyst, without a solvent or as needed in a proper solvent. On that occasion, the produced $R^1O(CH_2CH_2O)_m$OH is preferably distilled away under heating or under reduced pressure. The equilibrium is thus shifted to the product side, so that a higher yield can be achieved. The amount of water used is, for example, 2 to 3,000 equivalents, preferably 500 to 2,000 equivalents, more preferably 1,000 to 2,000 equivalents, relative to the number of moles of a compound represented by the general formula (5) although this is not particularly limited thereto.

Specific examples of the acid catalyst for use in the reaction of the [Step 3] include carboxylic acids such as formic acid, acetic acid, propionic acid, succinic acid, citric acid, tartaric acid, fumaric acid, malic acid, and trifluoroacetic acid, and inorganic acids such as hydrochloric acid, sulfuric acid, nitric acid, phosphoric acid, and perchloric acid, and sulfonic acids such as benzenesulfonic acid and p-toluenesulfonic acid, although this is not limited thereto. Specifically, a solid acid such as AMBERLYST SERIES made by Organo Corporation may be used. The amount of the acid catalyst used is, for example, 0.01 to 1,000 equivalents, preferably 0.01 to 500 equivalents, more preferably 0.01 to 200 equivalents, relative to the number of moles of a compound represented by the general formula (4) as reaction substrate.

In synthesizing a compound represented by the general formula (5) in the [Step 3], a proper solvent may be used as needed. In this case, a compound in a solid form represented by the general formula (4) produced in the previous step 2 may be dissolved in a solvent, and then reacted with water. Specific examples of the solvent for use include ethers such as THF and 1,4-dioxane, and aromatic hydrocarbons such as benzene, toluene, and xylene. The amount of the solvent used is, for example, 1 to 50 times, preferably 2 to 10 times, more preferably 2 to 5 times the mass of a compound represented by the general formula (5), although this is not particularly limited.

In the case of a compound represented by the general formula (5) in a solid form, the solid may be extracted for use prior to the subsequent step. In that case, the reaction liquid is, either directly or after concentration, dripped into a poor solvent to be crystallized. In the case of concentration; the concentration of a compound represented by the general formula (5) is adjusted to be, for example, 10 to 50 mass %, preferably 15 to 45 mass %, more preferably 20 to 40 mass %.

In concentration, solvent substitution with a good solvent for a compound represented by the general formula (5) may be performed for crystallization. In that case, examples of the good solvent include the same ones as exemplified in the step 2, although this is not limited thereto. These solvents may be used singly or in combinations of two or more. In that case, the mixing ratio is not particularly limited. The concentration after solvent substitution is, for example, 10 to 50 mass %, preferably 15 to 45 mass %, more preferably 20 to 40 mass %.

The poor solvent for use has a low solubility for the compound represented by the general formula (5). Examples of the poor solvent include the same poor solvents as exemplified in the step 2, although this is not limited thereto. The amount of the poor solvent used is, for example, 5 to 100 times, preferably 5 to 50 times, more preferably 5 to 20 times the mass of a compound represented by the general formula (5), although this is not particularly limited. The poor solvents may be used alone, or may be used by being mixed with a different solvent. Examples of the different solvent for mixing include the different solvents exemplified in the step 2, although this is not limited thereto.

In the [Step 3], after precipitation of solid by crystallization, the solid may be washed for purification as needed. Preferably the solvent for use in washing is the same poor solvent as described above, although this is not particularly limited, without particular limitation on the amount of the washing solvent used. The produced solid is dried under reduced pressure, so that a compound represented by the general formula (5) can be extracted as solid.

In the [Step 4], a compound represented by the general formula (5) can be reacted with ammonia or hydroxylamine to obtain a compound represented by the following general formula (6).

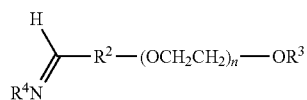

(6)

wherein $R^2$, $R^3$, and n are the same as defined in the general formula (5); and $R^4$ represents a hydrogen atom or a hydroxyl group.

In the reaction for synthesizing a compound represented by the general formula (6), a compound represented by the general formula (5) is reacted with ammonia or hydroxylamine without solvent or in a proper solvent as needed. Examples of the ammonia for favorable use in the reaction include liquefied ammonia and methanol solution of ammonia. The hydroxylamine for use is preferably a hydrochloride. The amount of ammonia or hydroxylamine used is, for example, 1 to 20 equivalents, preferably 1 to 10 equivalents, more preferably 1 to 5 equivalents, relative to the number of moles of a compound represented by the general formula (5) although this is not particularly limited thereto.

In synthesizing a compound represented by the general formula (6) in the [Step 4], the reaction liquid of a compound represented by the general formula (5) produced in the previous step 3 may be directly reacted with ammonia or hydroxylamine, or a proper solvent may be used as needed. In the case of using a solvent, a compound represented by the general formula (5) in a solid form produced in the previous step 3 may be dissolved in a solvent and then reacted with ammonia or hydroxylamine hydrochloride. Specific examples of the solvent include ethers such as THF and 1,4-dioxane, and aromatic hydrocarbons such as benzene, toluene, and xylene. The amount of the solvent used is, for example, 1 to 50 times, preferably 2 to 10 times, more preferably 2 to 5 times the mass of a compound represented by the general formula (6), although this is not particularly limited.

In the case of a compound represented by the general formula (6) in a solid form, the solid may be extracted for use prior to the subsequent step. In that case, the reaction liquid is, either directly or after concentration, dripped into a poor solvent to be crystallized. In the case of concentration, the concentration of a compound represented by the general formula (6) is adjusted to be 10 to 50 mass %, preferably 15 to 45 mass %, more preferably 20 to 40 mass %.

In concentration, solvent substitution with a good solvent for a compound represented by the general formula (6) may be performed for crystallization. In that case, examples of the good solvent include the same ones as exemplified in the step 2, although this is not limited thereto. These solvents may be used singly or in combinations of two or more. In that case, the mixing ratio is not particularly limited. The concentration after solvent substitution is, for example, 10 to 50 mass %, preferably 15 to 45 mass %, more preferably 20 to 40 mass %.

The poor solvent for use has a low solubility for a compound represented by the general formula (6). Examples of the poor solvent include the same poor solvents as exemplified in the step 2, although this is not limited thereto. The amount of the poor solvent used is, for example, 5 to 100 times, preferably 5 to 50 times, more preferably 5 to 20 times the mass of the compound represented by the general formula (6), although this is not particularly limited. The poor solvents may be used alone, or may be used by being mixed with a different solvent. Examples of the different solvent for mixing include the different solvents exemplified in the step 2, although this is not limited thereto.

In the [Step 4], after precipitation of a solid compound represented by the general formula (6) by crystallization, the solid may be washed for purification as needed. Preferably the solvent for use in washing is the same poor solvent as described above, although this is not particularly limited, without particular limitation on the amount of the washing solvent used. The produced solid is dried under reduced pressure, so that a compound represented by the general formula (6) can be extracted as solid.

In the [Step 5], a compound represented by the general formula (7) can be produced by a reduction reaction of a compound represented by the general formula (6).

In performing the reduction reaction of a compound represented by the general formula (6) in the [Step 5], the reaction liquid of a compound represented by the general formula (6) produced in the previous step 4 may be directly reacted, or a monohydric alcohol or a monovalent carboxylic acid having 1 to 5 carbon atoms or a mixture thereof may be added as needed for the reduction reaction. Alternatively, a compound represented by the general formula (6) in a solid form produced in the previous step 4 may be dissolved in a monohydric alcohol, a monovalent carboxylic acid or a mixture thereof and then subjected to the reduction reaction. Examples of the monohydric alcohol for use include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. Examples of the monocarboxylic acid include formic acid, acetic acid, and propionic acid. These solvents may be used singly or in combinations of two or more. In that case, the mixing ratio is not particularly limited. The amount of the solvent used is, for example, 10 to 3,000 equivalents, preferably 100 to 2,000 equivalents, more preferably 300 to 1,000 equivalents, relative to the number of moles of a compound represented by the general formula (6), although this is not particularly limited. In the viewpoints that use of an excess amount of carboxylic acid relative to amino groups is preferred, use of a solvent including a monovalent carboxylic acid in an amount of 300 to 3,000 equivalents relative to the number of moles of a compound represented by the formula (6) is particularly preferred.

In a reaction of producing an amino group by the hydrogen reduction reaction of C=N double bond, a produced primary amine reacts with a C=N double bond to generate a secondary amine and a tertiary amine as by-products. Use of a carboxylic acid as a reaction solvent causes a neutralization reaction with the produced primary amine, so that the generation of the secondary and tertiary amines is restricted. A monohydric alcohol is easily removed during purification, so that the use thereof is preferred. The use of both of these is more preferred.

The reduction reaction is performed under hydrogen atmosphere, using a hydrogenation catalyst. The catalyst for use may be a commonly used hydrogenation catalyst. Examples of the catalyst for suitable use include palladium carbon 10% (Tokyo Chemical Industry Co., Ltd.), a Raney cobalt catalyst ("R-400", Nikko Rica Corporation), a Raney nickel catalyst ("R-211" and "R-2311", Nikko Rica Corporation), a supported gold-palladium catalyst ("NTA-25", N. E. CHEMI-CAT Corporation), although this is not particularly limited. The amount of the catalyst used is, for example, 0.1 to 5 times, preferably 0.2 to 3 times, more preferably 0.3 to 2 times the mass of a compound represented by the general formula (6), although this is not limited thereto.

In the case of a reaction solvent without use of carboxylic acid, liquid ammonia, ammonia water, or methanol solution of ammonia may be added to a reaction system for suppression of the generation of a secondary amine and a tertiary amine. In that case, the amount of ammonia added is, for example, 0.1 to 100 times, preferably 0.2 to 80 times, more preferably 0.3 to 60 times the mass of a compound represented by the general formula (6), although this is not limited thereto.

The reaction temperature of a hydrogen reduction reaction is, for example, 0 to 150° C., preferably 20 to 130° C., more preferably 30 to 110° C. The reaction may be monitored by NMR, and when no change is observed in conversion ratio, the completion can be assumed. After completion of the reaction, filtration may be performed for removal of the used catalyst.

The reaction liquid of a compound represented by the general formula (7) may be subject to solvent substitution with a good solvent for a compound represented by the general formula (7) and dripped into a poor solvent for performing the crystallization for purification. In that case, examples of the good solvent include the same ones as exemplified in the step 2, although this is not limited thereto. These solvents may be used singly or in combinations of two or more. In that case, the mixing ratio is not particularly limited. The concentration after solvent substitution is, for example, 10 to 50 mass %, preferably 15 to 45 mass %, more preferably 20 to 40 mass %. In concentration, the concentration of a compound represented by the general formula (7) is adjusted to, for example, 10 to 50 mass %, preferably 15 to 45 mass %, more preferably 20 to 40 mass %.

The poor solvent for use has a low solubility for the compound represented by the general formula (7). Examples of the poor solvent include the same poor solvents as exemplified in the step 2, although this is not limited thereto. The amount of the poor solvent used is, for example, 5 to 100 times, preferably 5 to 50 times, more preferably 5 to 20 times the mass of the compound represented by the general formula (7), although this is not particularly limited. The poor solvents may be used alone, or may be used by being mixed with a different solvent. Examples of the different solvent for mixing include the different solvents exemplified in the step 2, although this is not particularly limited.

In the [Step 5], after precipitation of solid by crystallization, the solid may be washed for purification as needed. Preferably the solvent for use in washing is the same poor solvent as described above, although this is not particularly limited, without particular limitation on the amount of the washing solvent used. The produced solid is dried under reduced pressure, so that a compound represented by the general formula (7) can be extracted as solid.

After completion of the [Step 5], a step of separating impurities other than a compound represented by the general formula (7) using a strong acid cation exchange resin may be performed as an optional step. More specifically, after crude products in the [Step 5] is reacted with a strong acid cation exchange resin, the strong acid cation exchange resin is washed with water or monohydric alcohol having 1 to 5 carbon atoms for separation of substances other than a target compound represented by the general formula (7).

Specific examples of the strong acid cation exchange resin for suitable use include AMBERLITE series (IR120B, IR124B, 200CT, and 252) made by Organo Corporation, AMBERJET series (1020, 1024, 1060, and 1220) made by Organo Corporation, DIAION series (e.g. SK104, SK1B, SK110, SK112, PK208, PK212, PK216, PK218, PK220, PK228, UBK08, UBK10, UBK12, UBK510L, UBK530, and UBK550) by Mitsubishi Chemical Corporation, DOWEX series (50W×2 50-100, 50W×2 100-200, 50W×4 100-200, 50W×8 50-100, 50W×8 100-200, 50W×8 200-400, HCR-S, and HCR-W2(H)) made by Dow Chemical Co., although this is not limited thereto. The amount of the strong acid cation exchange resin used is, for example, 1 to 50 times, preferably 1 to 30 times, more preferably 1 to 20 times the mass of a compound represented by the general formula (7).

In the case of using a strong acid cation exchange resin, the strong acid cation exchange resin may be treated with an acid compound prior to use. Since commercially available strong acid cation exchange resins are often in an alkali metal sulfonate salt state, the pretreatment with an acid compound regenerates sulfo groups, so that the reaction efficiency can be improved. Examples of the acid compound for use include inorganic acids such as hydrochloric acid, sulfuric acid, nitric acid, phosphoric acid, and perchloric acid, although this is not limited thereto. The amount of the acid compound used is, for example, 1 to 15 times, preferably 1 to 10 times, more preferably 1 to 8 times the mass of the strong acid cation exchange resin. After treatment of the strong acid cation exchange resin with an acid compound, the acid compound is separated from the resin by water washing, and water is separated by a water-soluble organic solvent such as methanol and ethanol as needed.

Examples of the method for reacting a strong acid cation exchange resin and the crude product obtained in the [Step 5] include: flowing the solution of crude product in a column filled with the ion exchange resin to cause adsorption; and circulating the solution of crude product between a cartridge filled with the resin and the reaction tank for the [Step 5]; although this is not particularly limited.

The strong acid cation exchange resin with an adsorbed compound represented by the general formula (7) is washed with water or a monohydric alcohol having 1 to 5 carbon atoms, so that compounds other than the target substance can be separated. Examples of the monohydric alcohol having 1 to 5 carbon atoms include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol, although this is not limited thereto. In performing washing, water or a monohydric alcohol may be used alone, or a mixture of water and one or more alcohols or a mixture of two or more alcohols may be used. In that case, the mixing ratio is not particularly limited. The amount of water or a monohydric alcohol having 1 to 5 carbon atoms used is, for example, 1 to 30 times, preferably 1 to 20 times, more preferably 1 to 10 times the mass of the strong acid cation exchange resin for use, although this is not particularly limited.

The strong acid cation exchange resin with an adsorbed compound represented by the general formula (7) is reacted with a basic compound in water or a monohydric alcohol having 1 to 5 carbon atoms, so that a compound represented by the general formula (7) is extracted in the water or monohydric alcohol. In performing the reaction, water or the monohydric alcohol may be used alone, or a mixture of water and one or more alcohols or a mixture of two or more alcohols may be used. In that case, the mixing ratio is not particularly limited. Examples of the method for reacting a strong acid cation exchange resin and a basic compound include: flowing the solution of basic compound in a column filled with resin to cause reaction; and circulating the solution of basic compound between a cartridge filled with resin and the reaction tank for the [Step 5]; although this is not particularly limited.

Examples of the monohydric alcohol for use include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. The amount of water or a monohydric alcohol used is, for example, 1 to 30 times, preferably 1 to 20 times, more preferably 1 to 10 times the mass of the strong acid cation exchange resin for use, although this is not particularly limited.

As the basic compound, ammonia dissolved in water or an organic solvent (e.g. ammonia water and methanol solution of ammonia) may be suitably used, and primary, secondary and tertiary aliphatic amines, mixed amines, aromatic amines, and heterocyclic amines may be also used. Examples of the primary aliphatic amines include methylamine, ethylamine, n-propylamine, isopropylamine, n-butylamine, isobutylamine, sec-butylamine, tert-butylamine, and ethylene diamine; examples of the secondary aliphatic amines include dimethylamine, diethylamine, di-n-propylamine, diisopropylamine, di-n-butylamine, diisobutylamine, di-sec-butylamine; examples of the tertiary aliphatic amines include trimethylamine, triethylamine, tri-n-propylamine, triisopropylamine, tri-n-butylamine, tri-isobutylamine, and tri-sec-butylamine; examples of the mixed amines include dimethylethylamine, methylethylpropylamine, benzylamino, phenethylamine, benzyldimethylamine; specific examples of the aromatic amines and the heterocyclic amines include aniline derivatives (e.g. aniline, N-methylaniline, N-ethylaniline, N-propylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, and pyridine derivatives (e.g. pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), although this is not limited thereto. Alternatively an alkali aqueous solution such as potassium hydroxide and sodium hydroxide may be used as a basic compound. The amount of the basic compound used is, for example, 0.1 to 100 times, preferably 0.1 to 10 times, more preferably 0.1 to 5 times the mass of the resin for use.

By performing the preceding step 1, the preceding step 2, and the steps 1 to 5 of the present invention, a narrow molecular weight distribution polyethylene glycol derivative having an amino group at an end represented by the general formula (7) can be produced. In another aspect, the present invention relates to a narrow molecular weight distribution polyethylene glycol derivative having an amino group at an end represented by the general formula (7) produced by the production method.

In another embodiment, the present invention relates to a metal salt of a new acetal group-containing alcohol compound represented by the general formula (2) as a polymerization initiator for use in production method of the narrow molecular weight distribution polyethylene glycol derivative having an amino group at an end. Alternatively the present invention relates to a new acetal group-containing alcohol compound represented by the general formula (1) for use as raw material (starting material) of a polymerization initiator.

The definition, the production method, and the use of these compounds are omitted from description, with reference to the description in detail for the production method of the polyethylene glycol derivatives.

EXAMPLES

The present invention is specifically illustrated with reference to the following Examples and Comparative Examples, though the present invention is not limited to the following Examples. In the notation of molecular weight in Examples, the weight average molecular weight (Mw) and the number average molecular weight (Mn) are values in terms of polyethylene glycol measured by GPC. Measurement by GPC was performed under the following conditions:

Column: TSK gel Super AWM-H, Super AW-3000
Developing solvent: DMF (0.01 mol/L lithium bromide solution)
Column oven temperature: 60° C.
Sample concentration: 0.20 wt. %
Sample injection volume: 25 μl
Flow rate: 0.3 ml/min Synthesis Example 1

Synthesis of Compound Represented by Formula (1)

Synthesis Example 1-1

Synthesis of Compound Represented by Formula (1-1)

After placement of a stirring bar in a 500 mL four neck flask, 50.08 g of 3-chloropropionaldehyde diethyl acetal, 200 g of 2-methoxymethanol, and 0.38 g of AMBERLYST (registered trademark) 15DRY (Organo Corporation) were fed in to be reacted for 2 hours under conditions with an oil bath temperature of 70° C. and an internal pressure of 100 mmHg, while produced ethanol was distilled away under reduced pressure. After filtration of the AMBERLYST catalyst, a target substance was extracted with hexane and distilled to obtain a compound represented by a formula (1-1) with a yield rate of 78.0%. A reaction scheme is shown in the following.

$^1$H-NMR (500 MHz, DMSO-d6): δ=1.97 (2H, q), 3.24 (6H, s), 3.43 (4H, t), 3.51-3.56 (2H, m), 3.59-3.68 (4H, m), 4.69 (1H, t) ppm.

bp: 76° C. (0.23 mmHg).

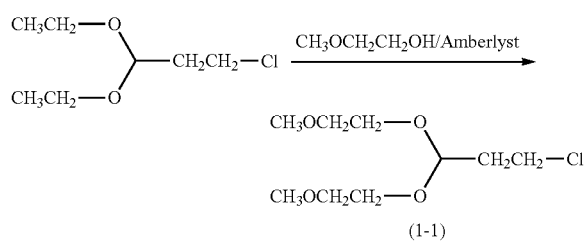

(1-1)

Synthesis Example 1-2

Synthesis of Compound Represented by Formula (1-2)

After placement of a stirring bar in a 500 mL four neck flask, 44.41 g of a compound represented by the formula (1-1), 36.0 g of potassium acetate, and 133.0 g of N-methylpyrrolidone were fed in to be reacted for 5 hours at 115° C. A target substance was extracted with ethyl acetate to obtain the crude product of a compound represented by the formula (1-2) with a crude yield rate of 73.1%. A reaction scheme is shown in the following.

$^1$H-NMR (500 MHz, DMSO-d6): δ=1.83 (2H, q), 1.99 (3H, s), 3.23 (6H, s), 3.42 (4H, t), 3.48-3.54 (2H, m), 3.60-3.66 (2H, m), 4.00 (2H, t), 4.63 (1H, t) ppm.

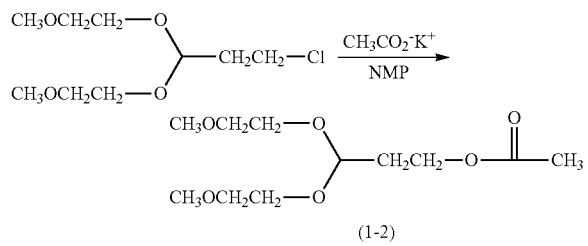

(1-2)

Synthesis Example 1-3

Synthesis of Compound Represented by Formula (1)

After placement of a stirring bar in a 1 L four neck flask, 33.30 g of a compound represented by the formula (1-2), 0.44 g of potassium carbonate, and 133 g of methanol were fed in to be reacted for 2 hours at room temperature. A target substance was concentrated with an evaporator and then distilled to obtain a compound represented by the formula (1) with a yield rate of 90.9%. A reaction scheme is shown in the following.

$^1$H-NMR (500 MHz, DMSO-d6): δ=1.66 (2H, q), 3.23 (6H, s), 3.40-3.44 (6H, m), 3.47-3.52 (2H, m), 3.58-3.64 (2H, m), 4.37 (1H, t), 4.63 (1H, t) ppm. bp: 102° C. (0.23 mmHg).

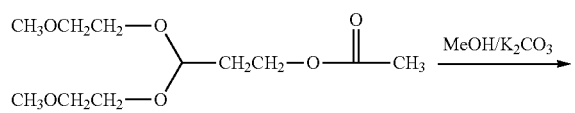

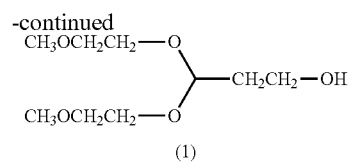

(1)

Synthesis Example 2

Synthesis of Compound Represented by General Formula (2)

In a glove box under nitrogen atmosphere, potassium hydride (in a mineral oil form, Kanto Chemical Co., Ltd.) was fed into a 100 mL three neck flask, washed with hexane, and then vacuum-dried for about 2 hours to obtain 1.12 g of potassium hydride. Into the flask, 21.46 g of distilled THF was added with a syringe, and 6.05 g of a compound represented by the formula (1) was dripped at normal temperature. After agitation for 1 hour at normal temperature, agitation was performed at 45° C. for 30 minutes, so that 27.82 g (1.03 mmol/g) of THF solution of a compound represented by the formula (2) was produced. A reaction scheme is shown in the following.

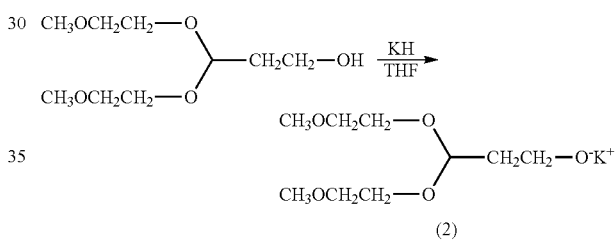

(2)

Synthesis Example 3

Synthesis of Compound Represented by General Formula (3)

A stirring bar was placed in a 500 mL four neck flask connected to a thermometer, a dripping funnel, and a Dimroth condenser. After the degree of vacuum in the device was held at 10 Pa or less, the internal part of the device was heated with an oil bath and a heat gun, so that the water content in the system was removed. Subsequently 1.69 g of the THF solution of a compound represented by the formula (2) and 140 g of distilled THF were added into a 2 L four neck flask under nitrogen stream. Into the dripping funnel, 20 g of ethylene oxide and 40 g of distilled THF were injected, to be dripped into the 500 mL four neck flask little by little. After confirming stabilization of the temperature in the 500 mL four neck flask, maturation was performed at 45 to 50° C. for 8 hours. A reaction scheme is shown in the following.

After completion of the reaction, the oil bath was detached and the reaction system was cooled to the room temperature. A small amount of the produced reaction liquid was sampled and quenched with acetic acid for measurement by GPC. The following results were obtained: Mw=6,100 and Mw/Mn=1.04.

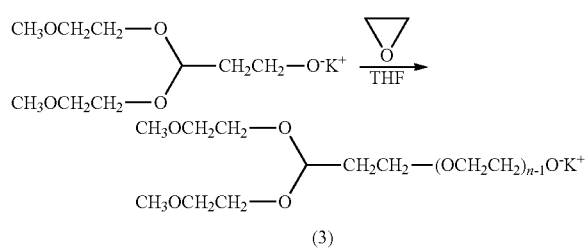

(3)

Synthesis Example 4

Synthesis of Compound Represented by General Formula (4)

Into the reaction liquid of a compound represented by the general formula (3), 2.41 g of 2-bromo ethyl methyl ether and 10.5 mL of THF solution of potassium tert-butoxide (1 mol/L) were added, and agitated for 5 hours under reflux. The reaction liquid was cooled and then concentrated to 25 wt. %. The concentrated liquid was transferred to a dripping funnel. Into a 500 mL beaker with a stirring bar therein, 201 g of a mixed solvent of ethyl acetate and hexane (volume ratio of 1:1) was injected. The concentrated liquid was dripped therein for 10 minutes, and maturation was performed for 20 minutes. The produced white powder was filtered and returned to the original beaker, to be washed with 99 g of a mixed solvent of ethyl acetate and hexane for 20 minutes. And the same washing operation was performed once more. A reaction scheme is shown in the following.

The produced white powder was vacuum-dried to obtain 18.6 g of a polymer (4). The following GPC measurement results were obtained: Mw=6,000 and Mw/Mn=1.05.

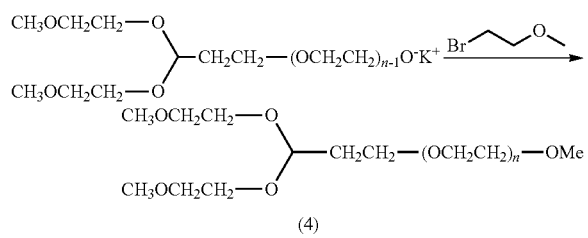

(4)

Synthesis Example 5

Synthesis of Compound Represented by General Formula (7A)

After placement of a stirring bar in a 100 mL four neck flask, 3.0 g of a compound represented by the formula (4), 8.0 g of acetic acid, 16.0 g of water were fed in to be reacted at 40° C. for 6 hours. Subsequently, 0.18 g of hydroxylamine hydrochloride, 0.23 g of sodium acetate, and 2.0 g of water were added and agitated for 1 hour. The reaction liquid was transferred to an autoclave, and 30 g of acetic acid, 30 g of methanol, 1.2 g of a palladium-carbon catalyst were fed in. Subsequently hydrogen gas (pressure: 10 kg/cm$^2$) was enclosed to be reacted at room temperature for 3 hours. After the pressure was returned to atmospheric pressure, the catalyst was filtered. The filtrate was transferred to a 100 ml round-bottom flask, and 30 g of toluene was added. Subsequently solvent substitution was performed with a rotary evaporator, and the precipitated salt was removed by filtration. Subsequently the solid content concentration of a compound represented by the general formula (7A) was adjusted to 25 wt. %.

Into a 100 mL beaker with a stirring bar placed therein, 30 g of a mixed solvent of ethyl acetate and hexane (volume ratio of 1:1) was injected. The concentrated liquid was dripped therein for 5 minutes, and maturation was performed for 20 minutes. The produced white powder was filtered and returned to the original beaker, to be washed with 15 g of a mixed solvent of ethyl acetate and hexane for 20 minutes. And the same washing operation was performed once more.

The produced white powder was vacuum-dried to obtain 2.5 g of a polymer (7A). The following GPC measurement results were obtained: Mw=5,700 and Mw/Mn=1.05.

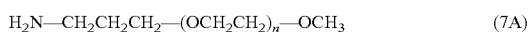

Mw: 5,700

Synthesis Example 6

Synthesis of Compounds Represented by the General Formulae (7B) to (7F)

Polymers (7B) to (7F) were synthesized by approximately the same operation as in the [Synthesis Example 3], except that the ratio of a compound represented by the general formula (2), ethylene oxide, and the polymerization solvent were changed. The analysis results are shown in Table 1.

TABLE 1

|  | Mw | Mw/Mn |
|---|---|---|
| Polymer (7A) | 5,700 | 1.05 |
| Polymer (7B) | 7,600 | 1.05 |
| Polymer (7C) | 8,800 | 1.06 |
| Polymer (7D) | 9,000 | 1.07 |
| Polymer (7E) | 10,200 | 1.06 |
| Polymer (7F) | 12,400 | 1.05 |

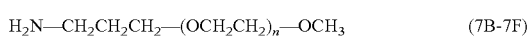

Mw: 7,600-12,400

Synthesis Example 7

Synthesis of Compounds Represented by the General Formulae (7G) to (7J)

Compounds represented by the general formulae (7G) to (7J) were synthesized by approximately the same operation as in the [Synthesis Example 4], except that the substrate (2-bromo ethyl methyl ether) was changed. The analysis results are shown in Table 2.

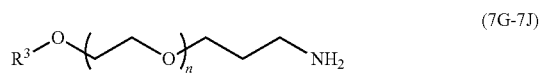

(7G-7J)

TABLE 2

|  | R$^3$ | Mw | Mw/Mn |
|---|---|---|---|
| Polymer (7G) | Ethyl group | 5,500 | 1.05 |
| Polymer (7H) | n-Propyl group | 5,700 | 1.06 |

TABLE 2-continued

|  | R³ | Mw | Mw/Mn |
|---|---|---|---|
| Polymer (7I) | Isopropyl group | 5,800 | 1.06 |
| Polymer (7J) | n-Butyl group | 5,400 | 1.07 |

Comparative Synthesis Example

A stirring bar and 0.07 g of potassium methoxide (Kanto Chemical Co., Ltd.) as a polymerization initiator was placed in a 500 mL four neck round-bottom flask connected to a thermometer, a dripping funnel, and a Dimroth condenser. After the degree of vacuum in the device was held at 10 Pa or less, the internal part of the device was heated with an oil bath and a heat gun, so that the water content in the system was removed.

Subsequently 40 μL of methanol (Tokyo Chemical Industry Co., Ltd.) and 140 g of distilled THF were injected in the four neck flask under nitrogen stream, and the mixture was agitated at room temperature until potassium methoxide was completely dissolved.

Into the dripping funnel, a mixed solution of 35 g of ethylene oxide and 60 g of distilled THF were injected, to be dripped into the four neck flask little by little, with the inner temperature being kept at 35° C. or lower. After dripping of the whole quantity, the mixture was agitated for 80 hours, with the inner temperature being kept at 50° C. or lower.

After confirming no change in conversion ratio of ethylene oxide, 0.06 g of acetic acid was added into the flask. After removal of ethylene oxide by nitrogen bubbling, the reaction liquid was transferred into a 500 mL round-bottom flask, and concentrated until solid is precipitated with a rotary evaporator. The crude product of polymer in an amount of 23 g was redissolved in 46 g of toluene, and transferred into a dripping funnel. Into a 500 mL beaker with a stirring bar therein, 138 g of isopropyl alcohol was injected. After dripping of the polymer solution for 10 minutes with a dripping funnel, maturation was performed for 20 minutes. The produced white powder was filtered and returned to the original beaker, to be washed with 69 g of isopropyl ether for 20 minutes. Then, the same washing operation was further performed twice.

The produced white powder was vacuum-dried to obtain 18.54 g of a polymer (comparative polymer 1). The following GPC measurement results were obtained: Mw=7,200 and Mw/Mn=1.16.

It is shown that, in Synthesis Examples 3 to 5 and Comparative Examples, while the latter required a long polymerization time of 80 hours, the former allowed the polymerization reaction to be completed within 8 hours by using the polymerization initiator soluble in THF. In other words, the method of the present invention achieves polymerization of ethylene oxide under mild conditions. Since no freeze drying is employed in purification of the polymer, the polymer can be produced by a simple method.

The polymer compound produced by the method of the present invention can be widely used as a starting material for synthesizing a block copolymer for use in medical supplies and cosmetic products including a field of drug delivery system.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for producing a narrow molecular weight distribution polyalkylene glycol derivative having an amino group at an end represented by a general formula (7) by using a compound represented by the following general formula (2) as a polymerization initiator:

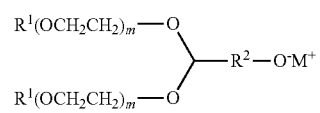

(2)

wherein R¹ each independently represents a linear, branched, or cyclic monovalent hydrocarbon group having 1 to 10 carbon atoms;

R² represents a linear or branched divalent hydrocarbon group having 1 to 5 carbon atoms;

m each independently represents an integer of 1 to 5; and

M represents sodium or potassium;

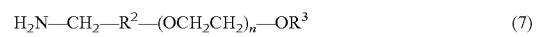

(7)

wherein R² is the same as defined in the general formula (2);

R³ represents a linear, branched, or cyclic monovalent hydrocarbon group having 1 to 20 carbon atoms; and n represents an integer of 1 to 450;

comprising the steps of:

a) reacting a compound represented by the formula (2) with ethylene oxide;

b) reacting a reaction product of the step a) with a compound represented by a general formula (8):

(8)

wherein R³ is the same as defined in the general formula (7);

k represents an integer of 0 to 5; and

X represents a halogen atom or a leaving group; and c) reductively aminating a reaction product of the step b).

2. A method for producing a narrow molecular weight distribution polyalkylene glycol derivative having an amino group at an end represented by a general formula (7) comprising the following steps of:

1) a step of reacting a compound represented by the following general formula (2) with ethylene oxide in an organic solvent to obtain a compound represented by the following general formula (3):

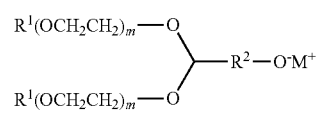

(2)

wherein R¹ each independently represents a linear, branched, or cyclic monovalent hydrocarbon group having 1 to 10 carbon atoms;

R² represents a linear or branched divalent hydrocarbon group having 1 to 5 carbon atoms;

m each independently represents an integer of 1 to 5; and

M represents sodium or potassium;

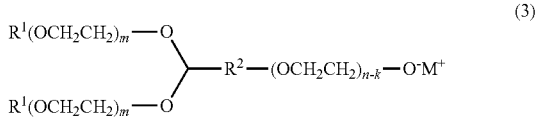

wherein $R^1$, $R^2$, m, and M are the same as defined in the general formula (2);
n represents an integer of 1 to 450; and
k represents an integer of 0 to 5;

2) a step of reacting a compound represented by the following general formula (3) with a compound represented by the following general formula (8) to obtain a compound represented by the following general formula (4):

$$R^3(OCH_2CH_2)_kX \qquad (8)$$

wherein k is the same as defined in the general formula (3);
$R^3$ represents a linear, branched, or cyclic monovalent hydrocarbon group having 1 to 20 carbon atoms; and
X represents a halogen atom or a leaving group;

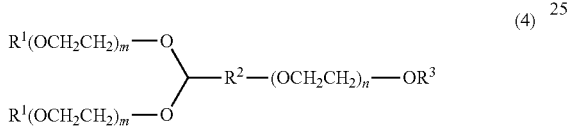

wherein $R^1$, $R^2$, m, and n, are the same as defined in the general formula (3); and
$R^3$ is the same as defined in the general formula (8);

3) a step of reacting a compound represented by the general formula (4) with water in the presence of an acid catalyst to obtain a compound represented by the following general formula (5):

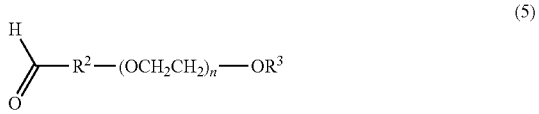

wherein $R^2$, $R^3$, and n are the same as defined in the general formula (4);

4) a step of reacting a compound represented by the general formula (5) with ammonia or hydroxylamine to obtain a compound represented by the following general formula (6):

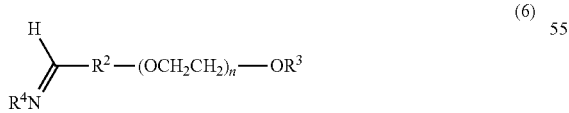

wherein $R^2$, $R^3$, and n are the same as defined in the general formula (5); and
$R^4$ represents a hydrogen atom or a hydroxyl group; and 5) a step of producing a compound represented by the following general formula (7) by a reduction reaction of a compound represented by the general formula (6):

$$H_2N-CH_2-R^2-(OCH_2CH_2)_n-OR^3 \qquad (7)$$

wherein $R^2$, $R^3$, and n are the same as defined in the general formula (6).

3. The method according to claim 2, wherein the organic solvent for use in the step 1) is a single solvent or a mixed solvent selected from the group consisting of cyclic ether compounds having 4 to 10 carbon atoms.

4. The method according to claim 2, wherein the step 1) is performed without an alcohol co-solvent.

5. The method according to claim 2, further comprising a preceding step of producing a compound represented by the general formula (2) by reacting a compound represented by the following general formula (1) with an alkali metal compound selected from M, $M^+H^-$, and $R^{21}O^-M^+$ (wherein M represents sodium or potassium, and $R^{21}$ represents an alkyl group having 1 to 6 carbon atoms) prior to the step 1):

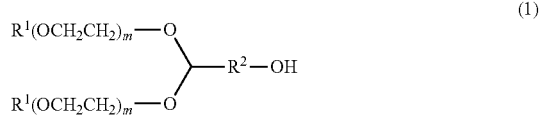

wherein $R^1$ represents a linear, branched, or cyclic monovalent hydrocarbon group having 1 to 10 carbon atoms;
$R^2$ represents a linear or branched divalent hydrocarbon group having 1 to 5 carbon atoms; and
m represents an integer of 1 to 5.

6. The method according to claim 5, wherein the reaction is performed so as to have a mass ratio between the compound represented by the general formula (1) and the compound represented by the general formula (2) of 0:100 to 20:80, after completion of the preceding step.

7. The method according to claim 5, further comprising a step of synthesizing a compound represented by the general formula (1) prior to the preceding step.

8. A narrow molecular weight distribution polyalkylene glycol derivative having an amino group at an end represented by a general formula (7) produced by the method according to claim 1:

$$H_2N-CH_2-R^2-(OCH_2CH_2)_n-OR^3 \qquad (7)$$

wherein $R^2$ represents a linear or branched divalent hydrocarbon group having 1 to 5 carbon atoms;
$R^3$ represents a linear, branched, or cyclic monovalent hydrocarbon group having 1 to 20 carbon atoms; and
n represents an integer of 1 to 450.

9. An acetal group-containing alcohol compound represented by the following general formula (1):

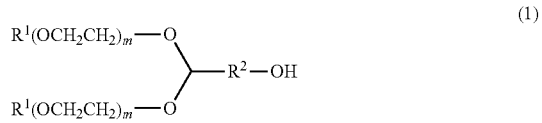

wherein $R^1$ each independently represents a linear, branched, or cyclic monovalent hydrocarbon group having 1 to 10 carbon atoms;
$R^2$ represents a linear or branched divalent hydrocarbon group having 1 to 5 carbon atoms; and
m each independently represents an integer of 1 to 5.

10. A metal salt of an acetal group-containing alcohol compound represented by the following general formula (2):

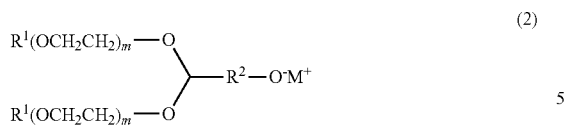

(2)

wherein $R^1$ each independently represents a linear, branched, or cyclic monovalent hydrocarbon group having 1 to 10 carbon atoms;

$R^2$ represents a linear or branched divalent hydrocarbon group having 1 to 5 carbon atoms;

m each independently represents an integer of 1 to 5; and

M represents sodium or potassium.

11. The method according to claim 3, wherein the step 1) is performed without an alcohol co-solvent.

* * * * *